United States Patent [19]
Liu et al.

[11] Patent Number: 5,603,919
[45] Date of Patent: Feb. 18, 1997

[54] LOW VOC HAIR SPRAY FIXATIVE COMPOSITIONS CONTAINING A TETRAMER

[75] Inventors: Kou-Chang Liu, Wayne; Colleen M. Rocafort, Lake Hiawatha, both of N.J.

[73] Assignee: ISP Investments Inc., Wilmington, Del.

[21] Appl. No.: 369,013

[22] Filed: Jan. 5, 1995

[51] Int. Cl.$^6$ .................................. A61K 7/11
[52] U.S. Cl. ................ 424/47; 424/45; 424/78.02; 424/70.11; 424/DIG. 1; 424/DIG. 2; 424/70.15; 424/70.16; 424/70.17; 514/957
[58] Field of Search .................... 424/47, DIG. 1, 424/DIG. 2, 78.02, 70.11, 45, 70.15, 70.16, 70.17; 514/957

[56] References Cited

U.S. PATENT DOCUMENTS

| | | | |
|---|---|---|---|
| 5,021,238 | 6/1991 | Martino et al. | 424/47 |
| 5,094,838 | 3/1992 | Benson et al. | 424/47 |
| 5,158,762 | 10/1992 | Pierce | 424/47 |
| 5,176,898 | 1/1993 | Goldberg et al. | 424/47 |

OTHER PUBLICATIONS

Johnsen, M. A. (1992). Spray Technology & Marketing/Jun., pp. 32–39.

Martino, G. T. et al. (1992). Spray Technology & Marketing/Mar., pp. 34–39.

*Primary Examiner*—Raj Bawa
*Attorney, Agent, or Firm*—Walter Katz; Marilyn J. Maue; Joshua J. Ward

[57] ABSTRACT

Low VOC hair spray fixative compositions containing a fixative which is a tetramer of vinyl pyrrolidone, vinyl caprolactam, 3-(N-dimethylaminopropyl) methacrylamide and a $C_8$-$C_{18}$ alkyl acrylamide or acrylate, in predetermined compositional ranges of each monomer, and molecular weight, are described. The hair spray compositions herein are clear and low in viscosity, and form a spray of relatively small particle size which spreads evenly on the hair of the user as clear films which exhibit an effective high humidity curl retention property, good stiffness, and low tack and short drying times.

6 Claims, No Drawings

1

LOW VOC HAIR SPRAY FIXATIVE COMPOSITIONS CONTAINING A TETRAMER

BACKGROUND OF THE INVENTION

1. Field of the Invention

This invention relates to low VOC hair spray fixative compositions, and, more particularly, to a fixative which is a tetramer of vinyl pyrrolidone (VP), vinyl caprolactam (VCL), 3-(dimethylaminopropyl) methacrylamide (DHAPHA) and a $C_8$-$C_{18}$ alkyl acrylamide or acrylate ($C_8$-$C_{18}$ AA).

2. Description of the Prior Art

U.S. Pat. No. 5,158,762 disclosed hair spray fixative compositions containing terpolymers obtained by polymerization of vinyl pyrrolidone, vinyl caprolactam and dimethylaminoethyl methacrylate (DMAEMA) (e.g. GAFFIX® VC-713, supplied by International Specialty Products). The monomer 3-(N-dimethylaminopropyl) methacrylamide was considered as a suitable ammonium derivative to replace dimethylaminoethyl methacrylate in the terpolymer, however, without further description.

Accordingly, it is an object of this invention to provide new and improved hair spray fixatives which are tetramers of VP, VCL, DMAPMA and $C_8$-$C_{18}$ AA monomers, in predetermined compositional ranges, and tetramer concentrates which are clear and low in viscosity, and which forms desirable spray patterns of small particle size.

Another object herein is to provide 55% or less VOC hair spray compositions having desirable hair care properties, including clear films which spread evenly on the hair of the user, effective high humidity curl retention, good stiffness, and low tack and short drying times.

SUMMARY OF THE INVENTION

In accordance with the invention, there is provided herein:

1. A hair fixative which is a tetramer of molecular weight 20,000 to 100,000, preferably 30,000 to 100,000 comprising 1–20 wt. %, preferably 5–15%, of vinyl pyrrolidone (VP), 60–95 wt. %, preferably 80–90%, of vinyl caprolactam (VCL), 1–10 wt. %, preferably 2.5–7.5%, of 3-(N-dimethylaminopropyl) methacrylamide (DMAPMA), and 1–10 wt. %, preferably 2–4%, of a $C_8$-$C_{18}$, alkyl acrylamide or methacrylamide, acrylate, or methacrylate ($C_8$-$C_{18}$ AA). The alkyl group may be straight, branched chain or cyclic. The preferred $C_8$-$C_{18}$ AA monomers are t-octyl acrylamide and n-octadecyl methacrylate.

2. A hair spray concentrate which is the tetramer described above homogeneous terpolymer resin in an aqueous, aqueous-alcoholic or alcoholic solvent, wherein the concentration of the terpolymer is about 10–50 wt. %, preferably 15–35%.

3. A 55% or less VOC (volatile organic compounds) pump spray composition, preferably 3–5% solids, which is a solution of about 1–10 wt. % of the tetramer of the invention, 55% or less ethanol, 0–5% adjuvants and the rest water.

4. A 55% or less VOC aerosol hair spray composition containing 1–10 wt. % tetramer, preferably 3–5%, 25 wt. % or less ethanol, and 35 wt. % or less of propellant, preferably dimethyl ether (DME), 0–5% adjuvants, preferably including a neutralizer and corrosion inhibitor, and the rest being water.

5. The tetramer of the invention may be prepared by a "one-pot" process wherein the four monomers are charged in a reaction vessel and polymerized by free radical solution polymerization.

6. The tetramer also may be made by a homogeneous polymerization process wherein the slowest reacting monomer of the tetramer (VCL) is precharged, optionally with small amounts of VP, DMAPMA and $C_8$-$C_{18}$ AA, and the faster reacting monomers (VP, DMAPMA and $C_8$-$C_{18}$ AA) are then introduced incrementally into the reactor at a predetermined feeding schedule so that the rate of disappearance of VP, DMAPMA and $C_8$-$C_{18}$ AA monomers substantially matches the rate of disappearance of VCL during the polymerization. This homogeneous process is described in detail in co-pending U.S. patent application Ser. No. 08/365,259, filed Dec. 28, 1994, which is incorporated by reference herein.

7. The tetramer described above which has a molecular weight of 20,000 to 100,000, preferably 30,000 to 70,000.

8. A 55% VOC or less pump or aerosol hair spray composition containing 1–10 wt. % of the tetramer which has an effective spray pattern and small particle size, forms clear, evenly spread films, a desirable high humidity curl retention property, good stiffness, and low tack and short drying times.

DETAILED DESCRIPTION OF THE INVENTION

A. TETRAMER FIXATIVE

The tetramer fixative of the invention may be prepared by a one-pot free radical solution polymerization process in alcohol, water or alcohol-water mixtures. Preferably the tetramer is made by solution polymerization in ethanol at a solids content of about 10–50%. Alternatively, the tetramers may be made by the homogeneous polymerization process described in detail in the above-mentioned copending patent applications. Tetramers prepared by homogeneous polymerization are homogeneous tetramers in contrast to those made by a one-pot process in which the tetramer product is a non-homogeneous tetramer.

The tetramer concentrate of the invention, i.e. the product of solution polymerization, contains the tetramer in a concentration of about 10–50 wt. % of the solution, preferably about 15–35%. The concentrate may be used directly for making hair spray compositions, both pump and aerosol formulations.

The presence of the $C_8$-$C_{18}$ alkyl acrylamide or acrylate monomer component of the tetramer fixative of the invention provides hair spray compositions having superior hold, reduced tack, lower dry time and stiffer films, than terpolymers without this monomer component.

The molecular weight of the tetramer of the invention suitably is 20,000 to 100,000, preferably 30,000 to 70,000, and, optimally about 50,000. At a molecular weight below 20,000, the tetramer does not provide suitable hold and above 100,000, it is not easily sprayable and forms only coarse particles which are unacceptable.

EXAMPLE 1

Preparation of VP/VCL/DMAPMA/t-Octyl Acrylamide Tetramer (wt. %—8.0/83.2/6.1/2.6)

Vinyl pyrrolidone (VP) (55.6 g), vinyl caprolactam (VCL) (577.5 g), dimethylaminopropyl methacrylamide (DMAPMA) (42.6 g), tert-octyl acrylamide (18.3 g) and ethanol (848.2 g) were charged into a 2-liter water-jacketed resin flask. The reaction flask was equipped with a condenser, a thermometer, a septum (for catalyst addition), an anchor-type metal stirrer, and a nitrogen sparge tube. Nitrogen was bubbled the solution while the resin flask was heated to 68° C. using hot water circulating through the jacketed flask. After an additional half-hour of degassing at reflux, a first shot of Lupersol 11 (0.25 ml) was injected into the flask. Subsequently, Lupersol 11 additions were made at 10, 40, 70, 100 minutes after the first addition. The reaction temperature was increased to 74° C. and 2 shots of Lupersol 554 M75 (0.12 ml) was then added at 240 and 330 minutes. The contents were allowed to react for an additional 5 hours and cooled to 35°–40° C. After neutralization with 12.5 g of $H_2SO_4$ (conc) the product was discharged as a 45% solution in ethanol.

The molecular weight of the tetramer obtained was 39,200.

EXAMPLE 2

Preparation of VP/VCL/DMAPMA/n-Octadecyl Methacrylate Tetramer (wt. %—7.8/81.4/6.0/4.8)

Vinyl pyrrolidone (55.6 g), vinyl caprolactam (577.5 g), dimethylaminopropyl methacrylamide (DMAPMA) (42.6 g), n-octadecyl methacrylate (33.9 g) and ethanol (867.2 g) were charged into a 2-liter water-jacketed resin flask. The reaction flask was equipped with a condenser, a thermometer, a septum (for catalyst addition), an anchor-type metal stirrer, and a nitrogen sparge tube. Nitrogen was bubbled through the solution while the resin flask was heated to 68° C. using hot water circulating through the jacketed flask. After an additional half-hour of degassing at reflexing, a first shot of Lupersol 11 (0.25 ml) was injected into the flask. Subsequently, Lupersol 11 additions were made at 10, 40, 70, 100, 140, 180 and 240 minutes after the first addition. The reaction temperature was then brought up to 75° C. and held for an additional 5 hours, then cooled to room temperature and discharged.

The molecular weight of the tetramer obtained was 41,100.

B. HAIR CARE COMPOSITIONS

The tetramer fixative of the invention may be used in conventional pump and aerosol hair spray formulations and also in multifunctional hair care products such as water-based, rinse-off hair styling and conditioning products, and in leave-on hair care products such as a mousse, and may be included as a concentrate or as a gel. Various actuator and packaging devices known in the art may be used therewith.

In a low VOC hair spray composition, the tetramer of the invention comprises about 1–10 wt. %, preferably 2–6%, and, most preferably, about 4%, by weight of the composition product, 55% or less of alcohol and propellant, the rest being water, and, optionally including up to 5% of adjuvant components such as vapor and liquid phase corrosion inhibitors, silicones, surface active agents, viscosity modifiers, dyes, chelating agents, distributing aids, pearlescent aids, opacifiers, perfumes, fatty alcohols, pH adjusting agents, and the like.

Pump Spray

The pump hair spray compositions of the invention were prepared by dissolving the tetramer concentrate in a suitable amount of ethanol and adding adjuvants and the requisite amount of water. The composition then was packaged into a high density polyethylene bottle fitted with a suitable pump actuator, e.g. a pump sprayer (160 ml) with 0.018×0.010 inch deep actuator (SEAQUIST EUROMIST II).

Aerosol Spray

The aerosol hair spray resin compositions of the invention were prepared from tetramer concentrate, ethanol, adjuvants including vapor and liquid phase corrosion inhibitors, suitable adjuvants, and the propellant.

The composition was packaged into a suitable aerosol can fitted with a SEAQUIST ST-74 valve with a (0.018" stem orifice, capillary body/0.015" vapor tap, and a 0.030" inner diameter tube). Alternatively a precisiion Aquasol valve system was used successfully.

Typical pump and aerosol spray formulations are shown in Table 1 below.

TABLE 1

Hair Spray Compositions

| Component | Pump Added | Wt. % Total | Component | Aerosol Added | Wt. % Total | |
|---|---|---|---|---|---|---|
| SD 40 Ethanol | 50.1 | — | SD 40 Ethanol | 16.33–21.33 | — | |
| Ethanol (100%) | — | 55 | Ethanol (100%) | — — | 20 | 25 |
| Water | 41 | 41 | Water | 41.4 | 41.4 | 41.4 |
| Tetramer | | | Tetramsor | | | |
| (45% solids in ethanol) | 8.9 | — | (45% solids in ethanol) | 6.67 | — | — |
| (solid) | — | 4 | (solid) | — | 3 | 3 |
| TOTAL | 100.00% | 100.00% | Corrosion Inhibitors | | | |
| | | | Liquid Phase* | 0.4 | 0.4 | 0.4 |
| | | | Vapor Phase** | 0.2 | 0.2 | 0.2 |
| | | | Propellant Dimethyl Ether | 30.00–35.00 | 35 | 30 |
| | | | TOTAL | 100.0  100.0 | 100.0 | 100.0 |

*MEA borate and MIPA borate (Monocar ® BE)
**Nitromethane, dimethyl oxazolidone (Oxaban ® A), or a dimethylamino-2-methyl-1-propane (DMAMP-80)

Typical hair care properties for the compositions of the invention are shown in Table 2 below.

TABLE 2

| Hair Care Property | | Pump | Aerosol |
|---|---|---|---|
| HHCR Hold (%) | (90 min) | 97 | 95 |
| | (4 hr.) | 97 | 92 |
| Particle size, DAV [v, 0.5]μ | | 98.57 | 56 |
| Stiffness | | 8.6 | 6.6 |
| Tack (sec) | | 28 | 13 |
| Dry time (sec) | | 46 | 23 |
| Film hardness | | 6H | HB |

The data in Table 2 shows that the films formed from the compositions herein have excellent hair fixative properties, particularly hold, stiffnesss, tack and dry times.

While the invention has been described with particular reference to certain embodiments thereof, it will be understood that changes and modifications may be made which are within the skill of the art. Accordingly, it is intended to be bound only by the following claims, in which:

What is claimed is:

1. A 55% or less, by wt., VOC pump hair spray composition consisting essentially of (i) about 1–10 wt. % of a hair spray fixative tetramer which forms clear, solutions in ethanol, water or ethanol-water mixtures consisting of the following monomers:

(a) vinyl pyrrolidone,
   (b) vinyl caprolactam,
   (c) 3-(N-dimethylaminopropyl) methacrylamide and
   (d) $C_8$-$C_{18}$ alkyl acrylamide in a compositional range of 1–10% of (a), 60–95% of (b), 1–10% of (c), and 1–10% of (d), by weight, having a weight average molecular weight of 20,000 to 100,000; (ii) 55 wt. % or less of ethanol; (iii) 0–5wt % adjuvants; and (iv) the rest water.

2. A 55% or less VOC pump hair spray composition according to claim 1 which includes about 3–5 wt. % of said tetramer.

3. A 55% or less, by wt., VOC aerosol hair spray composition consisting essentially (i) about 1–10 wt. % of a hair spray fixative tetramer which forms clear, solutions in ethanol, water or ethanol-water mixtures consisting of the following monomers:

(a) vinyl pyrrolidone,
   (b) vinyl caprolactam,
   (c) 3-(N-dimethylaminopropyl) methacrylamide and
   (d) $C_8$-$C_{18}$ alkyl acrylamide, in a compositional range of 1–10% of (a), 60–95% of (b), 1–10% of (c), and 1–10% of (d), by weight, having a weight average molecular weight of 20,000 to 100,000; (ii) 25 wt. % or less of ethanol; (iii) 0–5 wt. % adjuvants; (iv) 35 wt. % or less propellant other than ethanol; and (v) the rest water.

4. A 55% or less VOC aerosol hair spray composition according to claim 3 in which the adjuvants comprise about 0.2–0.6 wt. % of inhibitors.

5. A 55% or less VOC aerosol hair spray composition according to claim 3 which includes about 3–5 wt. % of said tetramer.

6. A 55% VOC aerosol hair spray composition according to claim 3 which includes about 4 wt. % of the tetramer, about 20–25 wt. % of ethanol, about 35–30 wt. % of dimethyl ether and 40.7 wt. % of water.

* * * * *